(12) United States Patent
Funk et al.

(10) Patent No.: US 7,960,490 B2
(45) Date of Patent: Jun. 14, 2011

(54) PROCESS FOR PREPARING COLOR-STABLE WATER-ABSORBING POLYMER PARTICLES WITH A LOW DEGREE OF NEUTRALIZATION

(75) Inventors: Rüdiger Funk, Niedernhausen (DE); Volker Braig, Weinheim-Lützelsachsen (DE)

(73) Assignee: BASF SE, Ludwigshafen (DE)

( * ) Notice: Subject to any disclaimer, the term of this patent is extended or adjusted under 35 U.S.C. 154(b) by 128 days.

(21) Appl. No.: 12/438,217

(22) PCT Filed: Sep. 17, 2007

(86) PCT No.: PCT/EP2007/059759
§ 371 (c)(1), (2), (4) Date: Feb. 20, 2009

(87) PCT Pub. No.: WO2008/034786
PCT Pub. Date: Mar. 27, 2008

(65) Prior Publication Data
US 2010/0001233 A1 Jan. 7, 2010

(30) Foreign Application Priority Data
Sep. 19, 2006 (EP) .................... 06120881

(51) Int. Cl.
*C08F 20/06* (2006.01)
(52) U.S. Cl. .............. 526/317.1; 502/402; 528/503
(58) Field of Classification Search ........... 528/503; 526/317, 317.1; 502/402
See application file for complete search history.

(56) References Cited

U.S. PATENT DOCUMENTS

| 4,873,299 A | 10/1989 | Nowakowsky et al. |
| 4,920,202 A | 4/1990 | Irie et al. |
| 5,668,252 A | 9/1997 | Yokoi et al. |
| 6,207,796 B1 | 3/2001 | Dairoku et al. |
| 7,285,615 B2 | 10/2007 | Adachi et al. |
| 2002/0120085 A1* | 8/2002 | Matsumoto et al. ........ 526/317.1 |
| 2004/0110914 A1* | 6/2004 | Nakahara et al. .......... 526/317.1 |
| 2008/0214749 A1 | 9/2008 | Weismantel et al. |

FOREIGN PATENT DOCUMENTS

| DE | 102005014291 | 9/2006 |
| EP | 0 238 050 | 9/1987 |
| EP | 0289338 | 11/1988 |
| EP | 1002806 | 5/2000 |
| EP | 1512417 | 3/2005 |
| EP | 1863852 | 12/2007 |
| WO | WO-2006/100300 | 9/2006 |

OTHER PUBLICATIONS

Cairncross et al. Journal of Applied Polymer Science, 58(8), 1995.*
Buchholz et al. (eds.), *Modern Superabsorbent Polymer Technology*, New York: Wiley-VCH, pp. 71-103 (1998).
Frank, "Superabsorbents", IN: *Ullmann's Encyclopedia of Industrial Chemistry*, 6th ed., vol. 35, New York: Wiley-VCH (2003).
International Preliminary Report on Patentability (English translation) for PCT/EP2007/059759, dated Apr. 7, 2009.
International Search Report and Written Opinion for PCT/EP2007/059759, dated Jan. 17, 2008.

* cited by examiner

*Primary Examiner* — David Wu
*Assistant Examiner* — Vu A Nguyen
(74) *Attorney, Agent, or Firm* — Marshall, Gerstein & Borun LLP

(57) ABSTRACT

The present invention relates to a process for producing water-absorbing polymeric particles by polymerizing a monomer solution comprising at least one ethylenically unsaturated acid-functional monomer less than 55 mol % neutralized and drying the resulting polymeric gel by means of a heated gas stream in at least two temperature zones.

15 Claims, No Drawings

PROCESS FOR PREPARING COLOR-STABLE WATER-ABSORBING POLYMER PARTICLES WITH A LOW DEGREE OF NEUTRALIZATION

CROSS-REFERENCE TO RELATED APPLICATIONS

This is the U.S. national phase of International Application No. PCT/EP2007/059759, filed Sep. 17, 2007, which claims the benefit of European Patent Application No. 06120881.5, filed Sep. 19, 2006.

The present invention relates to a process for producing water-absorbing polymeric particles by polymerizing a monomer solution comprising at least one ethylenically unsaturated acid-functional monomer less than 55 mol % neutralized and drying the resulting polymeric gel by means of a heated gas stream in at least two temperature zones.

Further embodiments of the present invention are discernible from the claims, the description and the examples. It will be appreciated that the hereinbefore identified and the hereinafter still to be more particularly described features of the subject matter of the present invention are utilizable not only in the particular combination indicated but also in other combinations without leaving the realm of the present invention.

Water-absorbing polymers are in particular polymers of (co)polymerized hydrophilic monomers, graft (co)polymers of one or more hydrophilic monomers on a suitable grafting base, crosslinked ethers of cellulose or of starch, crosslinked carboxymethylcellulose, partially crosslinked polyalkylene oxide or natural products that are swellable in aqueous fluids, such as guar derivatives for example. Such polymers are used as products capable of absorbing aqueous solutions to manufacture diapers, tampons, sanitary napkins and other hygiene articles, but also as water-retaining agents in market gardening.

The production of water-absorbing polymers is described for example in the monograph "Modern Superabsorbent Polymer Technology", F. L. Buchholz and A. T. Graham, Wiley-VCH, 1998, or in Ullmann's Encyclopedia of Industrial Chemistry, 6th edition, volume 35, pages 73 to 103.

The polymerization typically affords an aqueous polymeric gel which has to be dried. The drying of the polymeric gel is likewise disclosed in the monograph "Modern Superabsorbent Polymer Technology", F. L. Buchholz and A. T. Graham, Wiley-VCH, 1998, pages 87 to 93.

EP 289 338 A2 describes a process for drying polymeric gels with a gas stream which at least initially has a dew point in the range from 50 to 100° C.

EP 1 002 806 A1 discloses a process for producing water-absorbing polymers wherein a polymeric gel is dried in at least three sections.

Prior German patent application 102005014291.5 describes a drying process having a temperature profile.

The present invention has for its object to provide an improved process for producing water-absorbing polymeric particles of low degree of neutralization, in particular an improved drying of the aqueous polymeric gels generated during the process.

The present invention further has for its object to provide color-stable water-absorbing polymeric particles of low degree of neutralization, i.e., polymeric particles that do not yellow on prolonged storage.

We have found that this object is achieved by processes for producing water-absorbing polymeric particles by polymerization of a monomer solution comprising
a) at least one ethylenically unsaturated acid-functional monomer less than 55 mol % neutralized,
b) at least one crosslinker,
c) selectively one or more ethylenically and/or allylically unsaturated monomers copolymerizable with the monomers mentioned under a), and
d) selectively one or more water-soluble polymers,
the monomer solution being polymerized and the polymeric gel obtained being dried by means of a heated gas stream, which comprises effecting the drying in two or more temperature zones for which the gas inlet temperatures satisfy the condition $T_n$ greater than $T_{n+a}$, where the indices n and a are each a whole number greater than 0, the gas inlet temperature in the temperature zone $T_n$ being less than 175° C. and the temperature difference of the gas inlet temperatures of the temperature zones $T_n$ and $T_{n+a}$ being more than 10° C.

The indices indicate the chronological and/or spatial order of the temperature zones which the dryer feedstock traverses in ascending order. A temperature zone is a region in which the gas inlet temperature can be set independently.

The inventors discovered that polymeric gels dry completely differently depending on their degree of neutralization, and that the conditions under which the polymeric gel is dried have a decisive influence on the color stability of the water-absorbing polymeric particles produced.

The gas inlet temperature $T_n$ is preferably at least 120° C., more preferably at least 130° C., even more preferably at least 140° C. and most preferably at least 150° C. and preferably less than 173° C., more preferably less than 171° C., even more preferably less than 169° C. and most preferably less than 167° C.

The gas inlet temperature $T_{n+a}$ is preferably at least 100° C., more preferably at least 110° C., even more preferably at least 120° C. and most preferably at least 130° C. and preferably less than 160° C., more preferably less than 158° C., even more preferably less than 156° C. and most preferably less than 154° C.

The temperature difference of the gas inlet temperatures $T_n$ and $T_{n+a}$ is preferably more than 11° C., more preferably more than 12° C., even more preferably more than 13° C. and most preferably more than 14° C. and preferably less than 50° C., more preferably less than 40° C., even more preferably less than 35° C. and most preferably less than 30° C.

The water content of the polymeric gel to be dried on entry into the temperature zone $T_n$ is preferably at least 30% by weight, more preferably at least 40% by weight and most preferably 50% by weight and preferably up to 70% by weight, more preferably up to 65% by weight and most preferably up to 60% by weight.

The water content of the dried polymeric gel is preferably at least 2% by weight, more preferably at least 3% by weight and most preferably at least 5% by weight and preferably up to 10% by weight, more preferably up to 9% by weight and most preferably up to 8% by weight.

Water content is determined by EDANA (European Disposables and Nonwovens Association) recommended test method No. 430.2-02 "Moisture content".

In one preferred embodiment, the polymeric gel is admixed with a release agent before drying. Preferably, the release agent is added immediately before drying. Release agents reduce the sticking together of the gel particles. Suitable release agents are surfactants, for example having an HLB value of less than 12, such as sorbitan monooleate, inorganic powders, such as fumed silica, and organic powders, such as water-absorbing polymeric particles. The HLB value is a measure of the water or oil solubility of surfactants and can be determined by customary methods, for example in accordance with the methods indicated in "Surface Active Agents and Detergents", Volume 2, Interscience Publishers, Inc., pages 479 ff, or taken from reference tables. The powders typically have an average particle size of less than 300 μm, preferably less than 250 μm, more preferably less than 200 μm and most preferably less than 150 μm. Suitable water-absorbing polymeric particles are preferably polymeric particles as generated during the production of water-absorbing polymeric particles and screened out as undersize. Particle size can be determined for example by EDANA (European Disposables and Nonwovens Association) recommended test method No. 420.2-02 "Particle size distribution". Preference is given to using dried water-absorbing polymeric particles having a water content of less than 10% by weight, preferably less than 5% by weight and more preferably of less than 3% by weight.

The velocity of the gas stream flowing through the polymeric gel layer is preferably at least 0.5 m/s, more preferably at least 0.8 m/s and most preferably at least 1 m/s and preferably up to 5 m/s, more preferably up to 3 m/s and most preferably up to 2 m/s.

The gas to be used is not subject to any restrictions. The drying may utilize air, nitrogen or other gases that are inert under drying conditions. Air is preferred.

The drying residence time is preferably at least 10 minutes, more preferably at least 15 minutes and most preferably at least 20 minutes and preferably up to 100 minutes, more preferably up to 80 minutes and most preferably up to 60 minutes.

The drying is preferably effected at a pressure which is reduced, preferably by at least 0.5 mbar, more preferably by at least 2 mbar and most preferably at least 10 mbar, compared with the atmospheric pressure.

The process preferred for the present invention is a conveyor belt process (belt dryer). A belt dryer is a convective system of drying, for the particularly gentle treatment of through-airable products. The product to be dried is placed onto an endless conveyor belt which lets gas through, and is subjected to the flow of a heated gas stream, preferably air.

The drying gas is recirculated in order that it may become very highly saturated in the course of repeated passage through the product layer. A certain fraction of the drying gas, preferably not less than 10%, more preferably not less than 15% and most preferably not less than 20% and preferably up to 50%, more preferably up to 40% and most preferably up to 30% of the gas quantity per pass, leaves the dryer as a highly saturated vapor and carries off the water quantity evaporated from the product.

The size and design of the dryers depends on the product to be processed, the manufacturing capacity and the drying duty.

A belt dryer can be embodied as a single-belt, multibelt, multistage or multistory system. The present invention is preferably practiced using a belt dryer having at least one belt. One-belt dryers are very particularly preferred. To ensure optimum performance of the belt-drying operation, the drying properties of the water-absorbing polymers are individually determined as a function of the processing parameters chosen. The hole size and mesh size of the belt is conformed to the product. Similarly, certain surface enhancements, such as electropolishing or Teflonizing, are possible.

Any chain-guided or chainless belt system known to one skilled in the art can be used to ensure optimum conveying of product, examples being plate belts, thin sheet metal and endless plate belts, polymeric and metallic fabric belts.

To ensure economical drying of the water-absorbing polymers, the gas routing in the dryer is consistently designed for energy-efficient operation. Various gas-routing concepts are possible which have advantages with regard to drying characteristics and energy utilization. Energy-recovering systems can be used to utilize heat from the offgas stream to preheat the supplied fresh gas.

The dryer can be heated directly or indirectly via the various heating media such as steam, warm water, combustion gases, thermal oil or gas, preferably steam.

A uniform product feed is an essential prerequisite for optimal drying. Uniform product feed can be achieved through the use of swivelable and oscillating distributing belts, swing chutes or screws, vibration chutes or swing conveyors.

The polymeric gel to be dried is preferably applied to the belt of the belt dryer by means of a swivel belt. The feed height, i.e., the vertical distance between the swivel belt and the belt of the belt dryer, is preferably not less than 10 cm, more preferably not less than 20 cm and most preferably not less than 30 cm and preferably up to 200 cm, more preferably up to 120 cm and most preferably up to 40 cm.

The layer thickness on the belt dryer of the polymeric gel to be dried is preferably not less than 1 cm, more preferably not less than 2 cm and most preferably not less than 4 cm and preferably not more than 10 cm, more preferably not more than 9 cm and most preferably not more than 8 cm.

The belt speed of the belt dryer is preferably not less than 0.005 m/s, more preferably not less than 0.01 m/s and most preferably not less than 0.015 m/s and preferably up to 0.05 m/s, more preferably up to 0.03 m/s and most preferably up to 0.025 m/s.

In one preferred embodiment, the gas flow through the polymeric gel to be dried is upwardly in the upstream section of the belt dryer and downwardly in the downstream section of the belt dryer, the direction of flow being reversed at a water content of the polymeric gel of preferably at least 15% by weight, more preferably at least 20% by weight, even more preferably at least 25% by weight and most preferably at least 28% by weight and preferably not more than 45% by weight, more preferably not more than 35% by weight, even more preferably not more than 32% by weight and most preferably not more than 30% by weight.

Preferably, the gas velocity after flow reversal is elevated, preferably by at least 10%, more preferably by at least 30% and most preferably by at least 40% and preferably by up to 100%, more preferably by up to 80% and most preferably by up to 60%.

When flow through the belt dryer is upwardly to some extent at least, the gas velocity is preferably at least 5%, more preferably at least 8% and most preferably at least 10% and preferably up to 30%, more preferably up to 25% and most preferably up to 20% of the gas velocity needed to lift the polymeric gel off the belt.

The gas or air velocity at which the polymeric gel layer lifts off the belt (fluidization point) can be determined experimentally or computed by $$v_{max} = \sqrt{\frac{\rho_B \times g \times \Delta h}{CD}}$$

where $v_{max}$ is the maximum gas or air velocity at which the polymeric gel lifts off the belt, PB is the bulk density of the polymeric gel, g is the gravitational constant, Δh is the pressure drop through the polymeric gel layer, and $C_D$ is the gas or air drag coefficient.

Suitable monomers a) are for example ethylenically unsaturated carboxylic acids, such as acrylic acid, methacrylic acid, maleic acid, fumaric acid and itaconic acid, or derivatives thereof, such as acrylamide, methacrylamide, acrylic esters and methacrylic esters. Acrylic acid and methacrylic acid are particularly preferred. Acrylic acid is most preferable.

The monomers a) and especially acrylic acid comprise preferably up to 0.025% by weight of a hydroquinone half ether. Preferred hydroquinone half ethers are hydroquinone monomethyl ether (MEHQ) and/or tocopherols.

Tocopherol refers to compounds of the following formula:

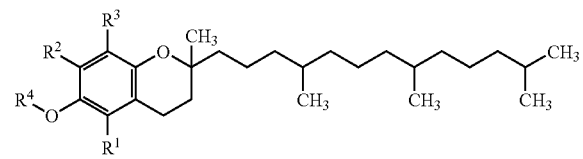

where $R^1$ is hydrogen or methyl, $R^2$ is hydrogen or methyl, $R^3$ is hydrogen or methyl and $R^4$ is hydrogen or an acyl radical of 1 to 20 carbon atoms.

Preferred $R^4$ radicals are acetyl, ascorbyl, succinyl, nicotinyl and other physiologically tolerable carboxylic acids. The carboxylic acids can be mono-, di- or tricarboxylic acids.

Preference is given to alpha-tocopherol where $R^1=R^2=R^3=$methyl, especially racemic alpha-tocopherol. $R^1$ is more preferably hydrogen or acetyl. RRR-alpha-tocopherol is preferred in particular.

The monomer solution comprises preferably not more than 130 weight ppm, more preferably not more than 70 weight ppm, preferably not less than 30 weight ppm, more preferably not less than 30 weight ppm and especially about 50 weight ppm of hydroquinone half ether, all based on acrylic acid, with acrylic acid salts being counted as acrylic acid. For example, the monomer solution can be produced using an acrylic acid having an appropriate hydroquinone half ether content.

Polymerization inhibitors can also be removed from the monomer solution by absorption, for example onto activated carbon.

The crosslinkers b) are compounds having at least two polymerizable groups which can be free-radically interpolymerized into the polymer network. Suitable crosslinkers b) are for example ethylene glycol dimethacrylate, diethylene glycol diacrylate, allyl methacrylate, trimethylolpropane triacrylate, triallylamine, tetraallyloxyethane, as described in EP 530 438 A1, di- and triacrylates, as described in EP 547 847 A1, EP 559 476 A1, EP 632 068 A1, WO 93/21237 A1, WO 2003/104299 A1, WO 2003/104300 A1, WO 2003/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures as described for example in DE 195 43 368 A1, DE 196 46 484 A1, WO 90/15830 A1 and WO 2002/32962 A2.

Useful crosslinkers b) include in particular N,N'-methylenebisacrylamide and N,N'-methylenebismethacrylamide, esters of unsaturated mono- or polycarboxylic acids of polyols, such as diacrylate or triacrylate, for example butanediol diacrylate, butanediol dimethacrylate, ethylene glycol diacrylate, ethylene glycol dimethacrylate and also trimethylolpropane triacrylate and allyl compounds, such as allyl (meth)acrylate, triallyl cyanurate, diallyl maleate, polyallyl esters, tetraallyloxyethane, triallylamine, tetraallylethylenediamine, allyl esters of phosphoric acid and also vinylphosphonic acid derivatives as described for example in EP 343 427 A2. Useful crosslinkers b) further include pentaerythritol diallyl ether, pentaerythritol triallyl ether, pentaerythritol tetraallyl ether, polyethylene glycol diallyl ether, ethylene glycol diallyl ether, glycerol diallyl ether, glycerol triallyl ether, polyallyl ethers based on sorbitol, and also ethoxylated variants thereof. The process of the invention utilizes di(meth)acrylates of polyethylene glycols, the polyethylene glycol used having a molecular weight between 300 and 1000.

However, particularly advantageous crosslinkers b) are di- and triacrylates of 3- to 15-tuply ethoxylated glycerol, of 3- to 15-tuply ethoxylated trimethylolpropane, of 3- to 15-tuply ethoxylated trimethylolethane, especially di- and triacrylates of 2- to 6-tuply ethoxylated glycerol or of 2- to 6-tuply ethoxylated trimethylolpropane, of 3-tuply propoxylated glycerol, of 3-tuply propoxylated trimethylolpropane, and also of 3-tuply mixedly ethoxylated or propoxylated glycerol, of 3-tuply mixedly ethoxylated or propoxylated trimethylolpropane, of 15-tuply ethoxylated glycerol, of 15-tuply ethoxylated trimethylolpropane, of 40-tuply ethoxylated glycerol, of 40-tuply ethoxylated trimethylolethane and also of 40-tuply ethoxylated trimethylolpropane.

Very particularly preferred for use as crosslinkers b) are diacrylated, dimethacrylated, triacrylated or trimethacrylated multiply ethoxylated and/or propoxylated glycerols as described for example in WO 2003/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. The triacrylates of 3- to 5-tuply ethoxylated and/or propoxylated glycerol are most preferred. These are notable for particularly low residual levels (typically below 10 weight ppm) in the water-absorbing polymer and the aqueous extracts of water-absorbing polymers produced therewith have an almost unchanged surface tension (typically not less than 0.068 N/m) compared with water at the same temperature.

Examples of ethylenically unsaturated monomers c) which are copolymerizable with the monomers a) are acrylamide, methacrylamide, crotonamide, dimethylaminoethyl methacrylate, dimethylaminoethyl acrylate, dimethylaminopropyl acrylate, diethylaminopropyl acrylate, dimethylaminobutyl acrylate, dimethylaminoethyl methacrylate, diethylaminoethyl methacrylate, dimethylaminoneopentyl acrylate and dimethylaminoneopentyl methacrylate.

Useful water-soluble polymers d) include polyvinyl alcohol, polyvinylpyrrolidone, starch, starch derivatives, polyglycols or polyacrylic acids, preferably polyvinyl alcohol and starch.

Polymerization inhibitors, which are preferred, require dissolved oxygen for optimum performance. Therefore, polymerization inhibitors may be freed of dissolved oxygen prior to polymerization by inertization, i.e. flowing an inert gas, preferably nitrogen, through them. The oxygen content of the monomer solution is preferably lowered to less than 1 weight ppm and more preferably to less than 0.5 weight ppm prior to polymerization.

The preparation of a suitable base polymer and also further useful hydrophilic ethylenically unsaturated monomers d) are described in DE 199 41 423 A1, EP 686 650 A1, WO 2001/45758 A1 and WO 2003/104300 A1.

Water-absorbing polymers are typically obtained by addition polymerization of an aqueous monomer solution with or without subsequent comminution of the polymeric gel. Suitable methods of making are described in the literature. Water-absorbing polymers are obtainable for example by gel polymerization in the batch process or tubular reactor and subsequent comminution in meat grinder, extruder or kneader (EP 445 619 A2, DE 198 46 413 A1), addition polymerization in kneader with continuous comminution by contrarotatory stirring shafts for example (WO 2001/38402 A1), addition polymerization on belt and subsequent comminution in meat grinder, extruder or kneader (DE 38 25 366 A1, U.S. Pat. No. 6,241,928), emulsion polymerization, which produces bead polymers having a relatively narrow gel size distribution (EP 457 660 A1).

The reaction is preferably carried out in a kneader as described for example in WO 2001/38402 A1, or on a belt reactor as described for example in EP 955 086 A2.

The acid groups of the polymeric gels obtained have been neutralized to an extent of less than 55 mol %, preferably to an extent of in the range from 10 to 55 mol %, more preferably to an extent of in the range from 20 to 50 mol % and even more preferably to an extent of in the range from 25 to 45 mol %, for which the customary neutralizing agents can be used, preferably alkali metal hydroxides, alkali metal oxides, alkali metal carbonates or alkali metal bicarbonates and also mixtures thereof. Instead of alkali metal salts it is also possible to use ammonium salts. Sodium and potassium are particularly preferred as alkali metals, but most preference is given to sodium hydroxide, sodium carbonate or sodium bicarbonate and also mixtures thereof. Neutralization is customarily achieved by admixing the neutralizing agent as an aqueous solution or else preferably as a solid material. For example, sodium hydroxide having a water content of distinctly below 50% by weight can be present as a waxy mass having a melting point of above 23° C. In this case, metering as piecegoods or melt at elevated temperature is possible.

Neutralization can be carried out after polymerization, at the polymeric gel stage. But it is also possible to neutralize up to 40 mol %, preferably from 10 to 30 mol % and more preferably from 15 to 25 mol % of the acid groups before polymerization by adding a portion of the neutralizing agent to the monomer solution and setting the desired final degree of neutralization only after polymerization, at the polymeric gel stage. The monomer solution can be neutralized by admixing the neutralizing agent. The polymeric gel may be mechanically comminuted, for example by means of a meat grinder, in which case the neutralizing agent can be sprayed, sprinkled or poured on and then carefully mixed in. To this end, the gel mass obtained can be repeatedly meat grindered for homogenization. Neutralization of the monomer solution to the final degree of neutralization is preferred.

The aqueous polymeric gels obtained are subsequently dried according to the process of the present invention which is described above.

The rest of the treatment of the dried polymeric gel is not important to the process of the present invention. The process of the present invention may further comprise the steps of grinding, sieving and/or postcrosslinking for example.

The dried polymeric gel is preferably ground and sieved, useful grinding apparatus typically including roll stands, hammer mills, pin mills or swing mills. The particle size of the sieved, dry polymeric gel is preferably below 1000 µm, more preferably below 900 µm and most preferably below 800 µm and preferably above 100 µm, more preferably above 150 µm and most preferably above 200 µm.

Very particular preference is given to a particle size (sieve cut) in the range from 106 to 850 µm. The particle size is determined according to EDANA (European Disposables and Nonwovens Association) recommended test method No. 420.2-02 "Particle size distribution".

The base polymers are then preferably surface postcrosslinked. Useful postcrosslinkers are compounds comprising groups capable of forming covalent bonds with two or more carboxylate groups of the polymeric gel. Suitable compounds are for example alkoxysilyl compounds, polyaziridines, polyamines, polyamidoamines, di- or polyglycidyl compounds, as described in EP 83 022 A2, EP 543 303 A1 and EP 937 736 A2, di- or polyfunctional alcohols, as described in DE 33 14 019 A1, DE 35 23 617 A1 and EP 450 922 A2, or 1'-hydroxyalkylamides, as described in DE 102 04 938 A1 and U.S. Pat. No. 6,239,230.

Useful surface postcrosslinkers are further said to include by DE 40 20 780 C1 cyclic carbonates, by DE 198 07 502 A1 2-oxazolidone and its derivatives, such as 2-hydroxyethyl-2-oxazolidone, by DE 198 07 992 A1 bis- and poly-2-oxazolidinones, by DE 198 54 573 A1 2-oxotetrahydro-1,3-oxazine and its derivatives, by DE 198 54 574 A1 N-acyl-2-oxazolidones, by DE 102 04 937 A1 cyclic ureas, by DE 103 34 584 A1 bicyclic amide acetals, by EP 1 199 327 A2 oxetanes and cyclic ureas and by WO 2003/031482 A1 morpholine-2,3-dione and its derivatives.

Postcrosslinking is typically carried out by spraying a solution of the surface postcrosslinker onto the polymeric gel or onto the dry base-polymeric powder. After spraying, the polymeric powder is thermally dried, and the crosslinking reaction may take place not only before but also during drying.

The spraying with a solution of the crosslinker is preferably carried out in mixers having moving mixing implements, such as screw mixers, paddle mixers, disk mixers, plowshare mixers and shovel mixers. Particular preference is given to vertical mixers and very particular preference to plowshare mixers and shovel mixers. Useful mixers include for example Lödige® mixers, Bepex® mixers, Nauta® mixers, Processall® mixers and Schugi® mixers.

Contact dryers are preferable, shovel dryers more preferable and disk dryers most preferable as apparatus in which thermal drying is carried out. Useful dryers include for example Bepex® dryers and Nara® dryers. Fluidized bed dryers can be used as well.

Drying may take place in the mixer itself, by heating the jacket or introducing a stream of warm air. It is similarly possible to use a downstream dryer, for example a tray dryer, a rotary tube oven or a heatable screw. But it is also possible for example to utilize an azeotropic distillation as a drying process.

Preferred drying temperatures are in the range from 50 to 250° C., preferably in the range from 50 to 200° C. and more preferably in the range from 50 to 150° C. The preferred residence time at this temperature in the reaction mixer or dryer is below 30 minutes and more preferably below 10 minutes.

The present invention further provides the water-absorbing polymeric particles obtainable according to the process of the present invention and also water-absorbing polymeric particles comprising i) at least one interpolymerized ethylenically unsaturated acid-functional monomer less than 55 mol % neutralized, ii) at least one interpolymerized crosslinker, iii) selectively one or more interpolymerized ethylenically and/or allylically unsaturated monomers copolymerizable with the monomers mentioned under i), iv) selectively one or more water-soluble polymers grafted at least partly with the monomers mentioned under i), and having a water content of less than 15% by weight and a Hunter 60 value of at least 60, the Hunter 60 value decreasing by less than 10% of the initial value during storage for one week at 70° C. and a relative humidity of 90%.

The degree of neutralization of the acid groups of the water-absorbing polymeric particles is preferably in the range from 10 to 55 mol %, more preferably in the range from 20 to 50 mol % and even more preferably in the range from 25 to 45 mol %.

Color measurement is carried out in accordance with the CIELAB procedure (Hunterlab, volume 8, 1996, No. 7, pages 1 to 4). In the CIELAB system, the colors are described via the coordinates L*, a* and b* of a three-dimensional system. L* indicates lightness, with L*=0 denoting black and L*=100 denoting white. The a* and b* values indicate the position of the color on the color axes red/green and yellow/blue respectively, where +a* represents red, −a* represents green, +b* represents yellow and −b* represents blue.

The color measurement complies with the three-range method of German standard specification DIN 5033-6.

The Hunter 60 value is a measure of the whiteness of surfaces and is defined as L*−3b*, i.e., the lower the value, the darker and the yellower a color is.

The Hunter 60 value is preferably at least 65, more preferably at least 68 and most preferably at least 70.

During storage for one week at 70° C. and a relative humidity of 90%, the Hunter 60 value decreases preferably by less than 12%, more preferably by less than 10% and most preferably by less than 8% of the initial value.

The b* value is preferably less than 10, more preferably less than 7, even more preferably less than 5 and most preferably less than 4.

During storage for one week at 70° C. and a relative humidity of 90%, the b* value increases preferably by less than 75%, more preferably by less than 50% and most preferably by less than 30% of the initial value.

The water content of the polymeric particles of the present invention is preferably at least 2% by weight, more preferably at least 3% by weight and most preferably at least 5% by weight and preferably up to 10% by weight, more preferably up to 9% by weight and most preferably up to 8% by weight.

The median particle size of the water-absorbing polymeric particles of the present invention is preferably in the range from 200 to 700 μm, more preferably in the range from 300 to 600 μm and most preferably in the range from 300 to 500 μm. The median particle size of the product fraction can be determined by means of EDANA (European Disposables and Nonwovens Association) recommended test method No. 420.2-02 "Particle size distribution", in which case the mass fractions of the sieve fractions are plotted in cumulative form and the median particle size is determined graphically. The median particle size is the mesh size value corresponding to an accumulated 50% by weight.

Preferably less than 10% by weight, more preferably less than 5% by weight and most preferably less than 2% by weight of the polymeric particles of the present invention have a particle size of less than 150 μm. An excessive proportion of small particles admittedly enhances the whiteness, but reduces the permeability of the swollen gel layer to further liquid.

The water-absorbing polymeric particles of the present invention typically have a centrifuge retention capacity (CRC) of at least 20 g/g, preferably at least 23 g/g and more preferably at least 25 g/g and customarily of less than 100 g/g. Centrifuge retention capacity (CRC) is determined by EDANA (European Disposables and Nonwovens Association) recommended test method No. 441.2-02 "Centrifuge retention capacity".

The present invention further provides processes for producing hygiene articles, in particular diapers, comprising the use of abovementioned water-absorbing polymeric particles of the present invention.

To determine their quality, the dried water-absorbing polymeric particles are tested using the hereinbelow described test methods.

Methods:

The measurements should, unless otherwise stated, be carried out at an ambient temperature of 23±2° C. and a relative humidity of 50±10%. The water-absorbing polymers are thoroughly commixed before measurement.

Water Content

The water content of the water-absorbing polymeric particles is determined in accordance with EDANA (European Disposables and Nonwovens Association) recommended test method No. 430.2-02 "Moisture content".

Centrifuge Retention Capacity (CRC Centrifuge Retention Capacity)

Centrifuge retention capacity of the water-absorbing polymeric particles is determined in accordance with EDANA (European Disposables and Nonwovens Association) recommended test method No. 441.2-02 "Centrifuge retention capacity".

Color Measurement

An LS-5100 Hunterlab LabScan colorimeter was used.

EXAMPLES

Examples 1 to 7

1235.1 g of a 37.3% by weight aqueous sodium acrylate solution, 529.31 g of acrylic acid, 1182.77 g of water, 1.32 g of urea, 1.32 g of 3-tuply ethoxylated glyceryl triacrylate were weighed into a 5000 ml glass beaker. The degree of neutralization was 40 mol %. This solution was then inertized with 100 l/h of nitrogen by means of a metal frit for 30 minutes. In addition, the solution was stirred (~100 rpm). During stirring, the monomer solution was cooled to 10° C. The cooling bath was removed shortly before the initiators were added. In succession 10.0 g of a 3% by weight aqueous solution of 2,2'-azobis(2-amidinopropane) dihydrochloride, 30.0 g of a 3% by weight aqueous solution of sodium persulfate, 7.0 g of a 3% by weight aqueous solution of hydrogen peroxide and 4.5 g of a 1% by weight aqueous solution of ascorbic acid were added. After the reaction had begun, the stirrer and the metal frit were removed from the reaction solution. After a reaction time of 30 minutes, the gel was removed and comminuted using a meat grinder equipped with a breaker plate (hole diameter 6 mm).

700 g of the comminuted gel are evenly distributed on a tray equipped with a mesh bottom and dried for 75 minutes in a circulating air drying cabinet (Heraeus UT 12, maximum circulation) at the temperature reported in the table.

After threefold grinding in a roll stand (Gebr. Baumeister LRC 125/70, slot widths 1000 μm, 600 μm, 400 μm), the polymer is passed through sieves to isolate a sieve cut between 850 and 100 μm.

Centrifuge retention capacity (CRC) was determined for the water-absorbing polymeric particles obtained. The results are summarized in table 1.

TABLE 1

Drying at different temperatures (degree of neutralization 40 mol %)

| Example | Temperature | Centrifuge retention capacity (CRC) |
|---|---|---|
| 1 | 160° C. | 29.5 g/g |
| 2 | 165° C. | 29.4 g/g |
| 3 | 170° C. | 26.9 g/g |
| 4 | 175° C. | 24.2 g/g |
| 5 | 180° C. | 24.0 g/g |
| 6 | 185° C. | 22.9 g/g |
| 7 | 190° C. | 20.8 g/g |

Centrifuge retention capacity (CRC) gets worse and worse with increasing drying temperature.

Examples 8 to 14

2478.79 g of a 37.3% by weight aqueous sodium acrylate solution, 275.41 g of acrylic acid, 192.91 g of water, 4.13 g of 3-tuply ethoxylated glyceryl triacrylate were weighed into a 5000 ml glass beaker. The degree of neutralization was 72 mol %. This solution was then inertized with 100 l/h of nitrogen by means of a metal frit for 30 minutes. In addition, the solution was stirred (~100 rpm). During stirring, the monomer solution was cooled to 10° C. The cooling bath was removed shortly before the initiators were added. In succession 10.0 g of a 3% by weight aqueous solution of 2,2'-azobis (2-amidinopropane) dihydrochloride, 30.0 g of a 3% by weight aqueous solution of sodium persulfate, 7.0 g of a 3% by weight aqueous solution of hydrogen peroxide and 4.5 g of a 1% by weight aqueous solution of ascorbic acid were added. After the reaction had begun, the stirrer and the metal frit were removed from the reaction solution. After a reaction time of 30 minutes, the gel was removed and comminuted using a meat grinder equipped with a breaker plate (hole diameter 6 mm).

700 g of the comminuted gel are evenly distributed on a tray equipped with a mesh bottom and dried for 75 minutes in a circulating air drying cabinet (Heraeus UT 12, maximum circulation) at the temperature reported in the table.

After threefold grinding in a roll stand (Gebr. Baumeister LRC 125/70, slot widths 1000 µm, 600 µm, 400 µm), the polymer is passed through sieves to isolate a sieve cut between 850 and 100 µm.

Centrifuge retention capacity (CRC) was determined for the water-absorbing polymeric particles obtained. The results are summarized in table 2.

TABLE 2

Drying at different temperatures (degree of neutralization 70 mol %)

| Example | Temperature | Centrifuge retention capacity (CRC) |
|---|---|---|
| 8 | 160° C. | 33.1 g/g |
| 9 | 165° C. | 33.8 g/g |
| 10 | 170° C. | 34.6 g/g |
| 11 | 175° C. | 36.2 g/g |
| 12 | 180° C. | 37.2 g/g |
| 13 | 185° C. | 38.9 g/g |
| 14 | 190° C. | 38.8 g/g |

As drying temperature rises, so does centrifuge retention capacity (CRC). This behavior is precisely the opposite of that observed for polymeric gels having a degree of neutralization of 40 mol %.

Polymeric gels of low degree of neutralization therefore have to be dried differently than polymeric gels of high degree of neutralization.

Examples 15 to 24

117.62 g of acrylic acid, 223.05 g of water and 52.28 g of a 50% by weight aqueous sodium hydroxide solution were mixed such that the temperature did not rise above 35° C. Then, 0.18 g of urea and 0.18 g of 3-tuply ethoxylated glyceryl triacrylate were weighed into a 600 ml glass beaker. The degree of neutralization was 40 mol %. This solution was then inertized with 100 l/h of nitrogen by means of a metal frit for 30 minutes. In addition, the solution was stirred (~100 rpm). During stirring, the monomer solution was cooled to 10° C. The cooling bath was removed shortly before the initiators were added. In succession 0.16 g of sorbitan monolaurate, 1.33 g of a 3% by weight aqueous solution of 2,2'-azobis(2-amidinopropane) dihydrochloride, 4.0 g of a 3% by weight aqueous solution of sodium persulfate, 0.93 g of a 3% by weight aqueous solution of hydrogen peroxide and 0.6 g of a 1% by weight aqueous solution of ascorbic acid were added. After the reaction had begun, the stirrer and the metal frit were removed from the reaction solution. After a reaction time of 30 minutes, the gel was removed and comminuted using a meat grinder equipped with a breaker plate (hole diameter 6 mm).

300 g of the comminuted gel were transferred into a cylindrical vessel equipped with a mesh bottom (mesh size of bottom plate: 350 µm, height: 11 cm, diameter: 10 cm) and dried with hot, unhumidified ambient air (air speed: 1.0 m/s) for a time $t_1$ at the temperature $T_1$ and if appropriate additionally for a time $t_2$ at the temperature $T_2$. The settings are summarized in table 3.

After threefold grinding in a roll stand (Gebr. Baumeister LRC 125/70, slot widths 1000 µm, 600 µm, 400 µm), the polymer was passed through sieves to isolate a sieve cut between 850 and 100 µm.

2.5 g of each sample were transferred into a small plastics Petri dish (height: 1.2 cm, internal diameter: 3.5 cm) and measured with a Macbeth Color Eye 2180 (Equation: CIELab, Illuminants: D65, Observer: 10°, CMC Ratio Lightness (I): 2., CMC Ratio Chromaticity (c): 1., Chromatic Wavelength: Auto, Block Sizes A1: 55.00, Block Sizes A2: 66.00, Block Sizes A3: 77.00) to determine the Hunter 60 value (HC 60) and the b* value. This measurement was repeated after storage for 7 and 14 days in a conditioning cabinet (90% relative humidity, 70° C.).

The values were used to compute the change after 7 days compared with the initial value.

The results are summarized in table 3.

TABLE 3

Drying with and without temperature profile

| Example | $t_1$ [min] | $T_1$ | $t_2$ [min] | $T_2$ | Water content | CRC [g/g] | ΔHC 60 | Δb* | Immediately after drying HC 60 | b* | After storage for one week HC 60 | b* | After storage for two weeks HC 60 | b* |
|---|---|---|---|---|---|---|---|---|---|---|---|---|---|---|
| 15 | 25 | 150° C. | | | 3.4 wt % | 32.2 | −18% | +81% | 71.402 | 4.485 | 58.426 | 8.124 | 34.496 | 12.845 |
| 16 | 25 | 160° C. | | | 3.2 wt % | 30.2 | −20% | +72% | 70.857 | 4.907 | 56.987 | 8.425 | 37.302 | 13.565 |
| 17 | 25 | 165° C. | | | 2.4 wt % | 28.6 | −18% | +63% | 70.569 | 5.067 | 57.945 | 8.269 | 38.846 | 13.645 |
| 18 | 25 | 170° C. | | | 1.7 wt % | 21.7 | −18% | +58% | 70.391 | 5.139 | 57.846 | 8.106 | 38.548 | 13.561 |
| 19 | 10 | 200° C. | 15 | 170° C. | 2.9 wt % | 31.4 | −24% | +109% | 73.805 | 3.828 | 56.328 | 7.984 | 39.027 | 13.000 |
| 20 | 10 | 200° C. | 20 | 170° C. | 2.0 wt % | 31.1 | −26% | +134% | 73.273 | 4.159 | 54.421 | 9.726 | 33.677 | 14.424 |
| 21 | 10 | 165° C. | 15 | 150° C. | 4.7 wt % | 40.3 | −8% | +70% | 71.947 | 3.973 | 65.984 | 6.735 | 49.057 | 10.177 |
| 22 | 10 | 170° C. | 15 | 150° C. | 3.6 wt % | 38.3 | −9% | +57% | 70.539 | 4.363 | 63.845 | 6.845 | 48.687 | 10.994 |
| 23 | 15 | 165° C. | 10 | 150° C. | 2.8 wt % | 31.0 | −7% | +52% | 70.335 | 4.595 | 65.240 | 6.963 | 44.896 | 10.302 |
| 24 | 15 | 170° C. | 10 | 150° C. | 2.7 wt % | 31.3 | −8% | +25% | 69.790 | 4.679 | 64.258 | 5.870 | 45.364 | 11.188 |

We claim:

1. A process for producing water-absorbing polymeric particles by polymerization of a monomer solution comprising
   a) at least one ethylenically unsaturated acid-functional monomer less than 55 mol % neutralized,
   b) at least one crosslinker,
   c) optionally one or more ethylenically and/or allylically unsaturated monomer copolymerizable with the monomers a), and
   d) optionally one or more water-soluble polymers, the monomer solution being polymerized and a polymeric obtained being dried by means of a heated gas stream, which comprises effecting the drying in two or more temperature zones for which gas inlet temperatures satisfy a condition $T_n$ greater than $T_{n+a}$, where the indices n and a are each a whole number greater than 0, the gas inlet temperature in the temperature zone $T_n$ being less than 175° C. and a temperature difference of the gas inlet temperatures of the temperature zones $T_n$ and $T_{n+a}$ being more than 10° C.

2. The process according to claim 1, wherein a water content of the polymeric gel on entry into the temperature zone $T_n$ is at least 30% by weight.

3. The process according to claim 1 wherein the polymeric gel comprises a release agent.

4. The process according to claim 1 wherein a layer thickness of the polymeric gel to be dried is less than 10 cm.

5. The process according to claim 1 wherein a velocity of the gas stream flowing through the polymeric gel layer is in the range from 0.5 to 5 m/s.

6. The process according to claim 1 wherein a residence time of the polymeric gel in the dryer is in a range from 10 minutes to 120 minutes.

7. The process according to claim 1 wherein a pressure prevailing during the drying is less than atmospheric pressure.

8. The process according to claim 1 wherein the drying is effected in a belt dryer.

9. The process according to claim 1 wherein the polymeric gel has a water content in a range from 2% to 10% by weight after drying.

10. Water-absorbing polymeric particles comprising
    i) at least one interpolymerized ethylenically unsaturated acid-functional monomer less than 55 mol % neutralized,
    ii) at least one interpolymerized crosslinker,
    iii) optionally one or more interpolymerized ethylenically and/or allylically unsaturated monomer copolymerizable with the monomers i),
    iv) optionally one or more water-soluble polymer grafted at least partly with he monomers i),
    and having a water content of less than 10%, by weight, and a Hunter 60 value of at least 60, the Hunter 60 value decreasing by less than 15% of an initial value during storage for one week at 70° C. and a relative humidity of 90%.

11. The polymeric particles according to claim 10 which exhibit a b* value of less than 10 which rises by less than 75% of an initial value during storage of one week at 70° C. and a relative humidity of 90%.

12. The polymeric particles according to claim 10 wherein a fraction of particles less than 150 μm in diameter is less than 10% by weight.

13. The polymeric particles according to claim 10 which exhibit a Centrifuge Retention Capacity (CRC) of at least 20 g/g.

14. The polymeric particles according to claim 10 which have a median particle size in a range from 300 to 600 μm.

15. A hygiene article comprising water-absorbing polymeric particles according to claim 10.

* * * * *